(12) United States Patent
Shioyama et al.

(10) Patent No.: US 9,163,209 B2
(45) Date of Patent: Oct. 20, 2015

(54) PIPETTE MEMBER AND CELL ISOLATION INSTRUMENT

(75) Inventors: Takahiro Shioyama, Tokyo (JP); Akane Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 13/541,183

(22) Filed: Jul. 3, 2012

(65) Prior Publication Data

US 2013/0017129 A1 Jan. 17, 2013

(30) Foreign Application Priority Data

Jul. 14, 2011 (JP) .................................. 2011-155636

(51) Int. Cl.
| | |
|---|---|
| *B01L 3/02* | (2006.01) |
| *C12M 3/00* | (2006.01) |
| *C12M 1/00* | (2006.01) |
| *C12M 1/33* | (2006.01) |
| *B01L 3/00* | (2006.01) |
| *G01F 25/00* | (2006.01) |
| *G01N 35/10* | (2006.01) |

(52) U.S. Cl.
CPC ................ *C12M 47/04* (2013.01); *B01L 3/021* (2013.01); *B01L 3/502* (2013.01); *C12M 45/02* (2013.01); *B01L 2300/047* (2013.01); *B01L 2300/0681* (2013.01); *B01L 2400/0487* (2013.01); *G01N 2035/103* (2013.01); *G01N 2035/1053* (2013.01)

(58) Field of Classification Search
USPC .......................................... 422/513; 73/1.74
See application file for complete search history.

(56) References Cited

U.S. PATENT DOCUMENTS

| | | | |
|---|---|---|---|
| 3,985,032 A * | 10/1976 | Avakian ...................... 73/863.25 |
| 4,483,825 A * | 11/1984 | Fatches ......................... 422/513 |
| 6,296,764 B1 * | 10/2001 | Guirguis et al. ........... 210/323.1 |
| 7,318,911 B2 * | 1/2008 | Smith ........................... 422/513 |
| 7,785,466 B1 * | 8/2010 | Smith ....................... 210/321.75 |
| 2005/0139704 A1 | 6/2005 | Liao et al. |
| 2006/0177352 A1 | 8/2006 | Ziegmann et al. |
| 2009/0239299 A1* | 9/2009 | Buss ............................. 435/374 |

FOREIGN PATENT DOCUMENTS

| | | |
|---|---|---|
| CN | 102123786 A | 7/2011 |
| EP | 1 688 181 A2 | 8/2006 |
| JP | 2003-235543 A | 8/2003 |
| JP | 2006-115781 A | 5/2006 |
| JP | 4156847 B2 | 7/2008 |
| JP | 2008-200028 A | 9/2008 |

OTHER PUBLICATIONS

The extended European Search Report for the related European patent application No. 12175545.8 dated Oct. 16, 2012.

(Continued)

*Primary Examiner* — Jill Warden
*Assistant Examiner* — Brittany Fisher
(74) *Attorney, Agent, or Firm* — Kenealy Vaidya LLP

(57) ABSTRACT

A pipette member to be attachable to a container capable of accommodating a tissue and a liquid, is used for isolating cells from the tissue by stirring, and includes: a cylinder member which includes a first opening that is to be accommodated in the container, and a second opening that is to be connected to a cell isolation apparatus, and in which a passage for communicating the first opening with the second opening is defined; and a filter member which is disposed inside the cylinder member, and which separates the passage into a first part that includes the first opening, and a second part that includes the second opening.

19 Claims, 6 Drawing Sheets

(56) References Cited

OTHER PUBLICATIONS

Chinese Office Action for the related Chinese Patent Application No. 201210240610.X dated Jan. 16, 2015.
Chunyan He et al.; "Laboratory tutorial of Medical Biochemistry"; Hubei Science and Technology Press; Sep. 30, 2010; p. 120; ISBN 978-7-5352-4551-9.
Japanese Office Action for the related Japanese Patent Application No. 2011-155636 dated Dec. 16, 2014.
Chinese Office Action for the related Chinese Patent Application No. 201210240610.X dated Aug. 7, 2015.

* cited by examiner

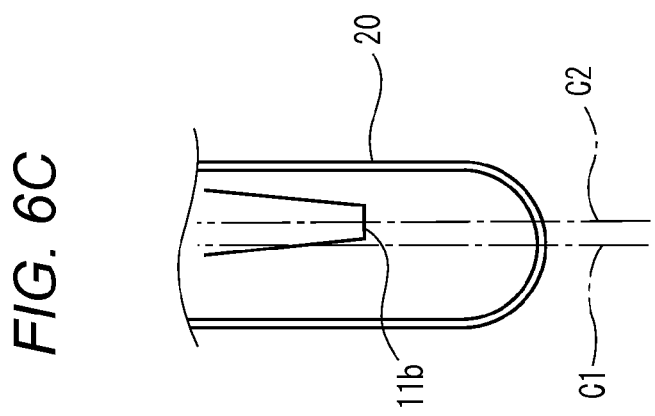
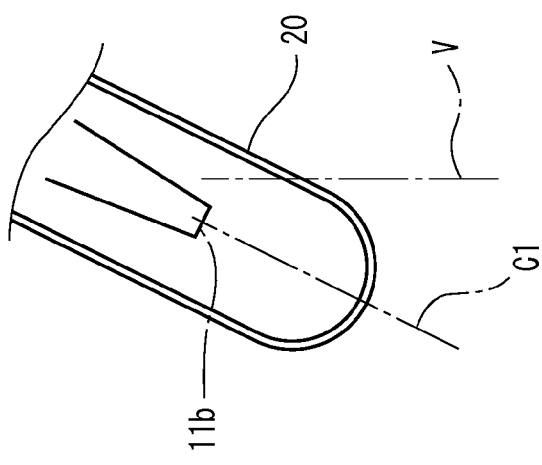
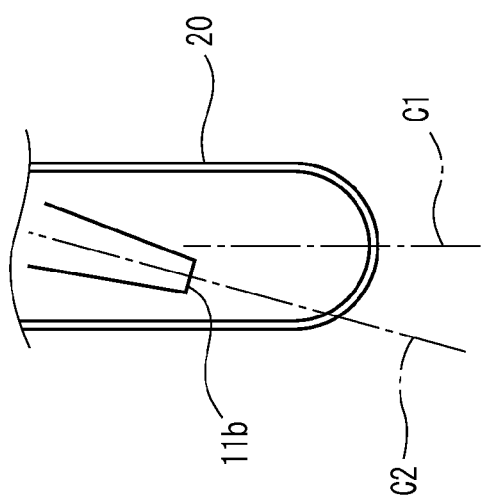

PIPETTE MEMBER AND CELL ISOLATION INSTRUMENT

BACKGROUND OF THE INVENTION

The present invention relates to a cell isolation instrument which can be used in the case where a pathological analysis is performed.

After a pathological specimen is prepared, a pathological analysis on a tissue slice is performed by a cytotechnologist or a pathologist. When cells are to be isolated from a tissue, the mincing process with using a blade is required. In order to obtain cell suspension containing isolated cells, moreover, a suspension which is obtained after the mincing process must be filtered through a filter. In order to obtain a cell suspension which is to be used in a pathological analysis, as described above, two steps of operation are required.

A skilled technique is required for preparing a specimen or performing a diagnosis by a cytotechnologist or a pathologist, and there is a possibility that a difference may be produced in the diagnosis result depending on the difference in technique. In the period from extraction of a tissue to diagnosis, procedures such as tissue fixation, section preparation, and staining are necessary, and a cytotechnologist or the like is restrained for a predetermined time period. Therefore, procedures which are to be performed before diagnosis are requested to be automatized.

Japanese Patent No. 4156847 discloses a device for mincing a tissue required for culturing cells. The device includes a cylinder member in which a metal mesh is disposed in each of upper and lower openings. A tissue piece is placed on the metal mesh, and a centrifugal separation process is performed on the cylinder member, whereby the tissue is minced.

According to the technique disclosed in Japanese Patent No. 4156847, the mincing process can be automatically performed, but procedures such as section preparation and staining cannot be automatized. Moreover, it is not considered that a cell suspension containing isolated cells is automatically recovered.

SUMMARY

It is therefore an object of the invention to provide at a low cost a cell isolation instrument which can efficiently recovery cells isolated from a tissue (living tissue).

In order to achieve the object, according to the invention, there is provided a pipette member to be attachable to a container capable of accommodating a tissue and a liquid, the pipette member used for isolating cells from the tissue by stirring, the pipette member comprising: a cylinder member which includes a first opening that is to be accommodated in the container, and a second opening that is to be connected to a cell isolation apparatus, and in which a passage for communicating the first opening with the second opening is defined; and a filter member which is disposed inside the cylinder member, and which separates the passage into a first part that includes the first opening, and a second part that includes the second opening.

A position of the filter member may be determined so that a first suction force which is applied for the stirring by the cell isolation apparatus causes only air to pass through the filter member, and, in a case where a second suction force which is larger than the first suction force is applied by the cell isolation apparatus, the liquid containing the isolated cells passes through the filter member.

The pipette member may further comprise a lid member which defines a part of the second opening. At least a part of the filter member may be in contact with the lid member.

The first opening may be smaller in diameter than the second opening.

A slit which communicates with the passage is formed in a vicinity of the first opening of the cylinder member.

A placement member on which the tissue can be placed may be provided in a vicinity of the first opening of the cylinder member.

In a state where the pipette member is attached to the container, the first opening may be placed in a position which is deviated from a central axis of the container.

The filter member may allow a material which is smaller than isolated cells, to pass through.

In order to achieve the object, according to the invention, there is also provided a cell isolation instrument comprising: a container capable of accommodating a tissue and a liquid; and a pipette member attached to the container, and used for isolating cells from the tissue by stirring, the pipette member comprising: a cylinder member which includes a first opening that is accommodated in the container, and a second opening that is to be connected to a cell isolation apparatus, and in which a passage for communicating the first opening with the second opening is defined; and a filter member which is disposed inside the cylinder member, and which separates the passage into a first part that includes the first opening, and a second part that includes the second opening.

A position of the filter member may be determined so that a first suction force which is applied for the stirring by the cell isolation apparatus causes only air to pass through the filter member, and, in a case where a second suction force which is larger than the first suction force is applied by the cell isolation apparatus, the liquid containing the isolated cells passes through the filter member.

The first opening may be placed in a position which is deviated from a central axis of the container.

In a state where the cell isolation instrument is attached to the cell isolation apparatus, a central axis of the container may be inclined with respect to a vertical direction.

A dried reagent may be placed in a bottom portion of the container.

BRIEF DESCRIPTION OF THE DRAWINGS

FIGS. 6A, 6B and 6C are partial enlarged views showing modifications of the cell isolation instrument of FIG. 1.

DETAILED DESCRIPTION OF EMBODIMENTS

Hereinafter, an embodiment of the invention will be described in detail with reference to the accompanying drawings.

Figure 1:
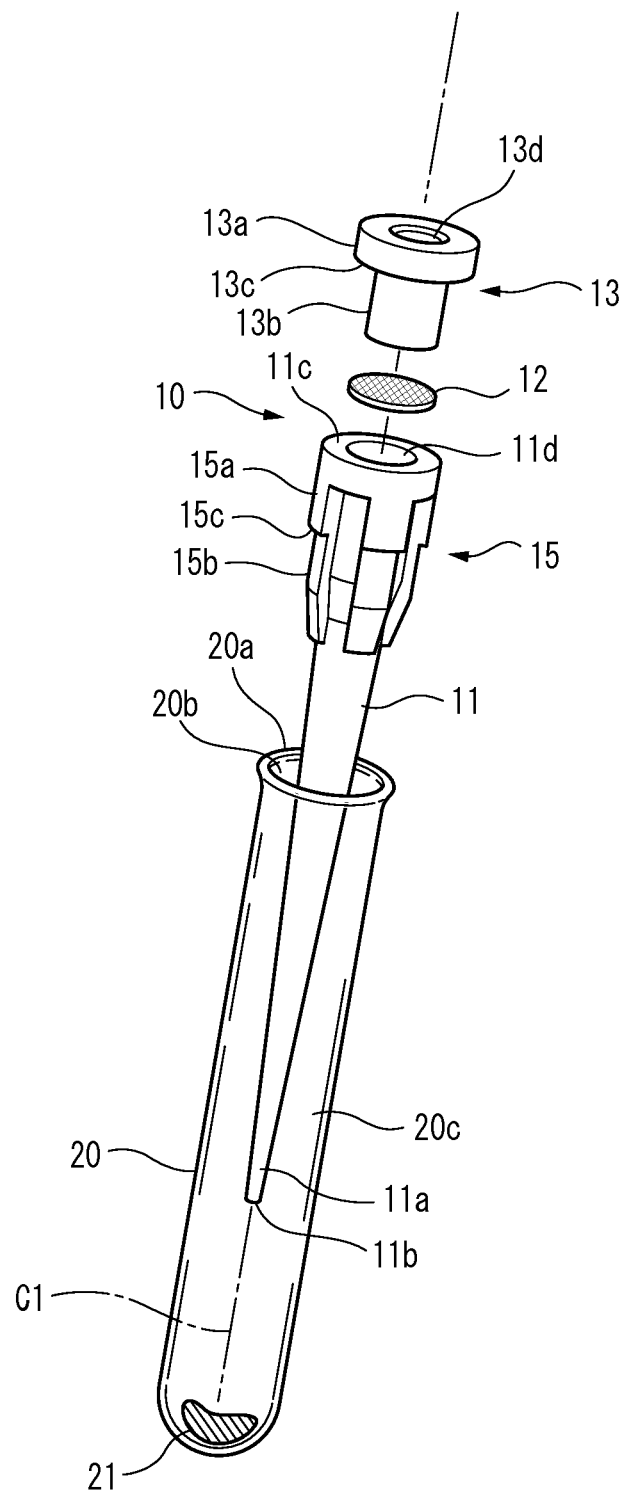
FIG. 1 is an exploded perspective view showing a cell isolation instrument of an embodiment of the invention.
Figure 2:
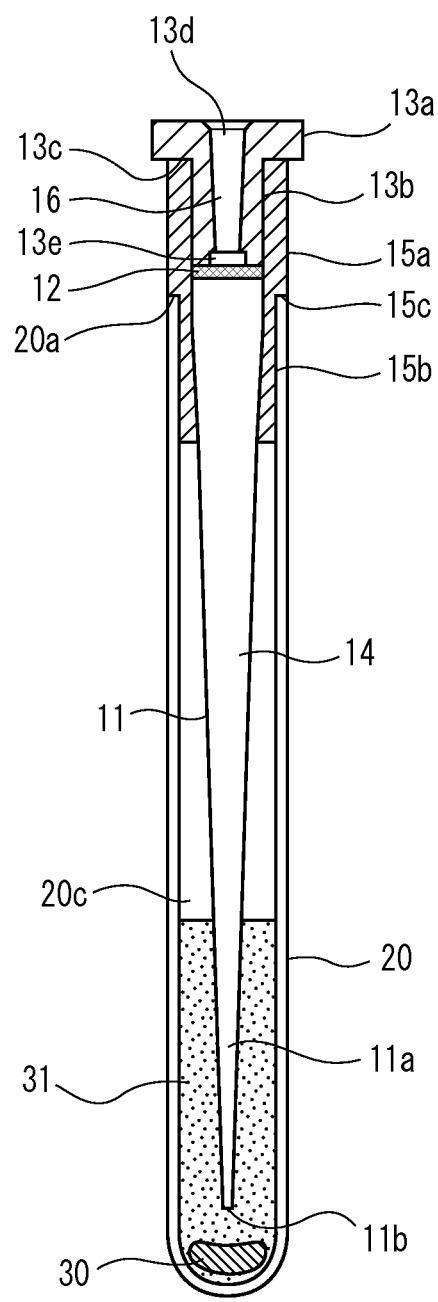
FIG. 2 is a longitudinal sectional view showing a state where the cell isolation instrument of FIG. 1 is assembled.

FIG. 1 shows a state where a cell isolation instrument of an embodiment of the invention is disassembled, and FIG. 2 shows a state where the device is assembled. The cell isolation instrument includes a pipette member 10 and a container 20. The both components are formed by a resin material or the like which is noncytotoxic.

The pipette member 10 includes a body 11, a filter 12 (filter member), and a lid member 13.

The body 11 is a hollow cylindrical member in which a tip end portion 11a has a tapered shape. An opening 11b (first opening) is formed in the tip end (lower end) of the body 11, and an opening 11d is formed in the upper end surface 11c. The openings 11b, 11d communicate with each other through a passage 14 which is formed inside the body 11.

A holding member 15 is disposed in an upper end portion of the body 11. The holding member 15 has a large-diameter portion 15a and a small-diameter portion 15b. A step 15c is defined in the interface between the large-diameter portion 15a and the small-diameter portion 15b. The large-diameter portion 15a includes the upper end surface 11c. The role of the holding member 15 will be described later.

The lid member 13 is a cylindrical member having a large-diameter portion 13a and a small-diameter portion 13b. A step 13c is defined in the interface between the large-diameter portion 13a and the small-diameter portion 13b. An opening 13d (second opening) is formed in the upper end surface including the large-diameter portion 13a, and an opening 13e is formed in the lower end surface including the small-diameter portion 13b. The openings 13d, 13e communicate with each other through a passage 16 which is formed inside the lid member 13.

The filter 12 is formed by a material which is noncytotoxic, and has mesh openings which allow a liquid containing isolated cells (cells in which nuclei are isolated) to pass therethrough. In the embodiment, a nylon mesh having mesh openings of 50 μm is used as the filter 12, and adhered or welded to the lid member 13 so as to cover the opening 13e.

As shown in FIG. 2, the filter 12 and the small-diameter portion 13b of the lid member 13 are inserted into the opening 11d to be attached to the body 11, so that the body 11 and the lid member 13 constitute the cylinder member in the invention. The step 13c of the lid member 13 is adhered or welded to the upper end surface 11c of the body 11. In this state, the passage 14 (first part) of the body 11 and the passage 16 (second part) of the lid member 13 communicate with each other through the filter 12 which is placed in a predetermined position. The detail of "predetermined position" will be described later.

The container 20 is a cylindrical member which has an opening 20b in the upper end surface 20a, and in which a lower end portion is configured as a round bottom. The container 20 is transparent so that the hollow internal space 20c is visible. The internal space 20c communicates with the opening 20b.

A reagent 21 containing a surfactant, an RNA (ribonucleic acid) remover, and a fluorescent dye/pigment is accommodated on the bottom of the internal space 20c in a state where the reagent 21 is dried or freeze-dried. When a tissue 30 and cell treatment solution 31 (liquid) which are to be used in the cell isolation process are loaded into the internal space 20c, the reagent 21 dissolves in the cell treatment solution 31. Preferably, a solution in which the osmotic pressure is equal to that of a living body, such as PBS (phosphate buffer solution) is used as the cell treatment solution 31. In parallel with a below-described cell isolation process by stirring, nuclei isolation of tissue cells by the surfactant, RNA removal by the RNA remover, and staining of isolated DNA cell nuclei by the fluorescent dye/pigment can be performed. This enables that, after recovery by a cell isolation apparatus which will be described later, measurement by a fluorescent analyzer (flow cytometer) or the like is performed. Therefore, rapid diagnosis can be realized.

As shown in FIG. 2, the pipette member 10 is attached to the container 20 in which the tissue 30 and the cell treatment solution 31 are accommodated in the internal space 20c. Specifically, the body 11 of the pipette member 10 is inserted from the opening 20b of the container 20 into the internal space 20c until the upper end surface 20a of the container 20 abuts against the step 15c of the holding member 15. In this state, the outer circumferential surface of the small-diameter portion 15b of the holding member 15 abuts against the inner surface of the container 20.

Namely, the holding member 15 is fitted to an upper end portion of the container 20, so that a tip end portion 10a of the pipette member 10 is placed in a predetermined position in the internal space 20c of the container 20. Specifically, the tip end (opening 11b) of the body 11 is placed on the central axis C1 (see FIG. 1) of the container 20, and opposed to the bottom of the internal space 20c via a constant gap. In the state shown in FIG. 2, the loaded tissue 30 is placed between the tip end of the body 11 and the bottom of the internal space 20c. The tip end portion 11a of the body 11 is immersed in the loaded cell treatment solution 31.

Next, the cell isolation process in which the cell isolation instrument of the embodiment is used will be described with reference to FIGS. 3A and 3B.

Figure 3:
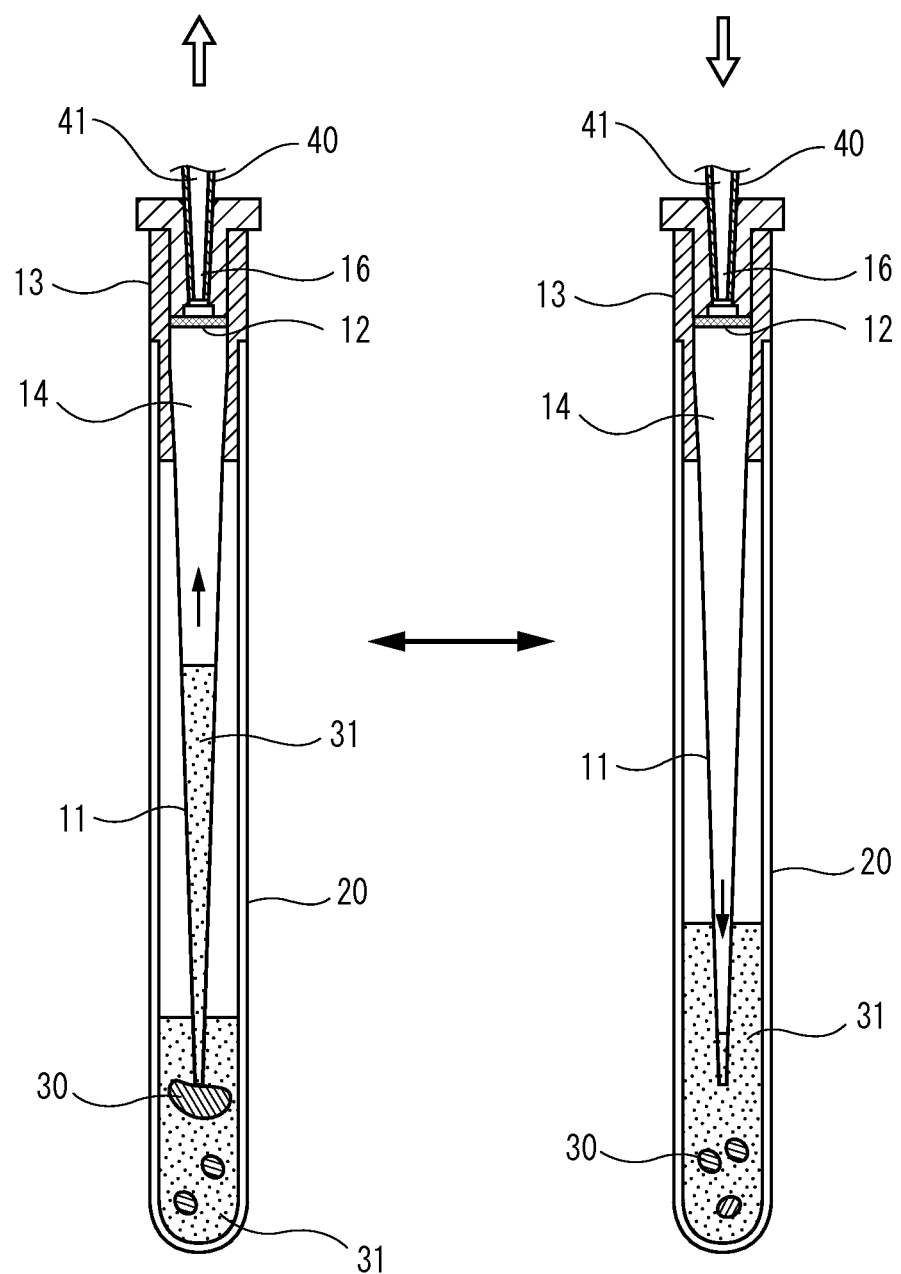
FIGS. 3A and 3B are longitudinal sectional views showing states where a stirring process is performed by using the cell isolation instrument of FIG. 1.

As shown in FIGS. 3A and 3B, first, an upper end portion of the cell isolation instrument which is assembled as shown in FIG. 2 is attached to a lower end portion of a nozzle 40 of the cell isolation apparatus. Specifically, a passage 41 of the nozzle 40 and the passage 16 of the lid member 13 communicate with each other in an air-tight and liquid-tight manner through an adequate engagement structure.

Although not illustrated in detail, the cell isolation apparatus includes a pump mechanism which is connected to the nozzle 40. The cell isolation apparatus is configured so that a controller controls the pump mechanism based on stirring conditions (stirring intensity, repetition number, duration, and the like) which are set by the user, and a pressurized state and a depressurized state can be made. In the pressurized state, air is blown out from the nozzle 40 through the passage 41, and, in the depressurized state, air is sucked into the nozzle 40 through the passage 41.

When the pressurized state and the depressurized state are repeated, the tissue 30 and the cell treatment solution 31 (containing the reagent 21) in the container 20 can be stirred by the pipette member 10 connected to the nozzle 40.

FIG. 3A shows a state where the cell isolation apparatus makes the depressurized state. A predetermined suction force (first suction force) acts on the pipette member 10, and the cell treatment solution 31 in the container 20 is sucked up into the pipette member 10. Part of the cell treatment solution 31 is raised in the passage 14, and the tissue 30 is sucked to the tip end (opening 11b) of the pipette member 10. At this time, part of the tissue is smashed by collision with the tip end of the pipette member 10.

FIG. 3B shows a state where the cell isolation apparatus makes the pressurized state. A predetermined pressure is applied to the pipette member 10, and the cell treatment solution 31 in the passage 41 is ejected from the opening 11b to be returned to the internal space 20c of the container 20. At this time, the tissue which is sucked to the opening 11b is returned into the cell treatment solution 31 while part of the tissue is smashed by shock caused by the ejection.

By repeating the above-described suction and ejection processes, the tissue 30 is gradually finely smashed to enter a minced state. When the stirring process is performed for a constant time period, a suspension 32 (see FIG. 4) containing isolated cells can be obtained.

The isolated cells are used in a pathological analysis. In addition to the isolated cells, however, unwanted minced tissue pieces are suspended in the suspension 32. In order to use only the isolated cells in the analysis, a step of filtering out tissue pieces which are larger than the isolated cells is necessary.

In the embodiment, while the cell isolation instrument remains to be connected to the nozzle 40, a suction force (second suction force) which is larger than that acting in the stirring process is caused by the cell isolation apparatus to act on the pipette member 10.

Figure 4:
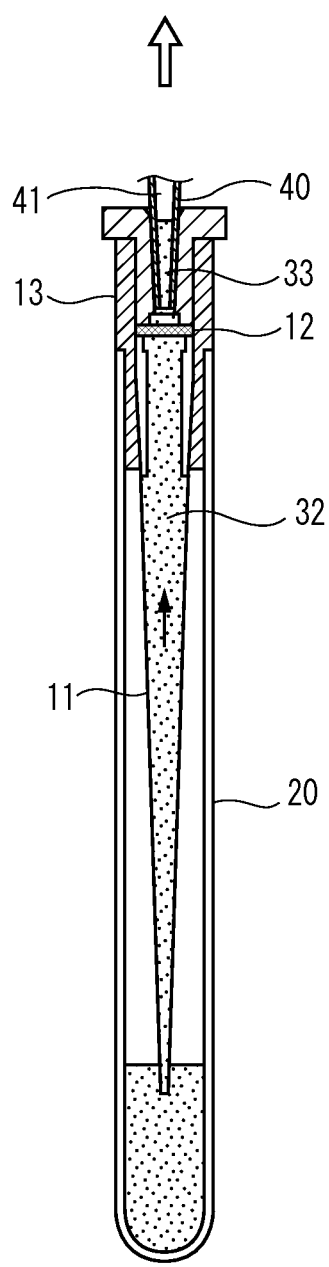
FIG. 4 is a longitudinal sectional view showing a state where a filtered cell suspension is recovered by using the cell isolation instrument of FIG. 1.

As shown in FIG. 4, then, the suspension 32 in the container 20 is sucked into the pipette member 10, and raised in the passage 14. When the cell isolation apparatus continues the suction, the suspension 32 reaches the filter 12 which separates the passage 14 from the passage 16. When the suspension 32 passes through the filter 12, unwanted tissue pieces are filtered out, and a cell suspension 33 containing desired isolated cells is obtained in the passage 16. When the sucking operation is further continued, the cell suspension 33 is recovered to the cell isolation apparatus, and then used in an analyzing process such as a fluorescence analysis by using a flow cytometer.

Namely, the cell isolation process by stirring, and the process of recovering the isolated cells by filtering the suspension can be performed while the same cell isolation instrument is connected to the nozzle 40 of the cell isolation apparatus. The working efficiency can be largely improved as compared with a related-art process in which such a suspension is transferred to another container, and filtration is then performed. Moreover, the process of recovering the isolated cells by filtration can be automated.

The pipette member 10 of the embodiment has the simple configuration where the filter 12 and the lid member 13 are attached to the body 11. The above-described effects can be achieved at low component and production costs. The pipette member 10 can be discarded in a state where the filter 12 and the lid member 13 are attached to the body 11, and it is possible to prevent the user from directly contacting with the suspension. Furthermore, it is possible to prevent foreign substances from entering in the suspension. Therefore, the safety is high.

Hereinafter, above-described "predetermined position" of the filter 12 will be described. In the cell isolation apparatus, as described above, the two kinds of suction forces for stirring and filtration act on the pipette member 10. In the embodiment, the position of the filter 12 is determined so that the liquid which enters the passage 14 is not caused to reach the filter 12 by the suction force for stirring, and caused to pass through the filter 12, only by the suction force for filtration.

As shown in FIG. 3A, namely, the suction force applied during stirring causes only air to pass through the filter 12, and the liquid passes through the filter 12 in the case where a suction force which is larger than that during stirring is applied as shown in FIG. 4. According to this configuration, not only the cell isolation process by stirring, but also the process of recovering the isolated cells by filtration can be easily automated. During stirring, that is, the filter 12 is not immersed in the liquid, only air passes through the filter 12, and hence the stirring resistance can be reduced as far as possible. Therefore, the load which is applied to the pump mechanism of the cell isolation apparatus during the stirring operation can be suppressed to minimum.

In the embodiment, since the filter 12 allows a material which is smaller than the isolated cells, to pass through, it is possible to collect only cells which have undergone necessary nuclei isolation. Therefore, the cell isolation process can be performed accurately and smoothly.

In the embodiment, since the reagent 21 which is dried is placed in a bottom portion of the container 20 (the bottom of the internal space 20c), when the tissue 30 and the cell treatment solution 31 (liquid) is accommodated in the container 20, the reagent 21 dissolves in the liquid, and a process which is the object of the reagent 21 can be performed in parallel with the cell isolation process by stirring.

Next, modifications of the cell isolation instrument of the embodiment will be described with reference to FIGS. 5A to 6C.

Figure 5A:
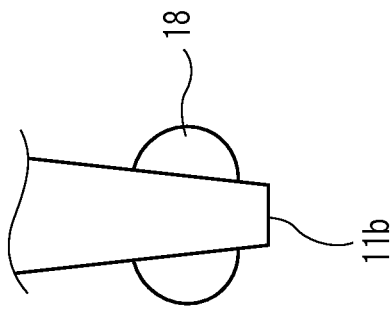
FIGS. 5A, 5B and 5C are partial enlarged views showing modifications of the cell isolation instrument of FIG. 1.

A configuration may be employed where, as shown in FIG. 5A, a slit 17 is formed in the vicinity of the opening 11b in the tip end of the pipette member 10.

As shown in FIG. 3A, in the case where the suction force for stirring acts on the pipette member 10, the opening 11 is sometimes completely blocked by the tissue 30 sucked to the pipette member 10. According the configuration of the modification, even in such a case, the cell treatment solution 31 flows through the slit 17, and therefore a desired suction process can be performed. Furthermore, the load which is applied to the pump mechanism of the cell isolation apparatus that generates the suction force can be reduced.

Figure 5B:
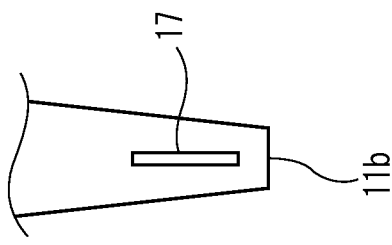

The position and shape of the slit 17 are not particularly limited as far as the slit is formed in the vicinity of the opening 11b and does not impede the flow of the cell treatment solution 31. The slit may be continuous to the opening 11b as shown in FIG. 5A, or independent from the opening 11b as shown in FIG. 5B. Namely, it is requested that the pipette member has a portion through which a liquid can pass, in addition to the opening 11b.

Figure 5C:
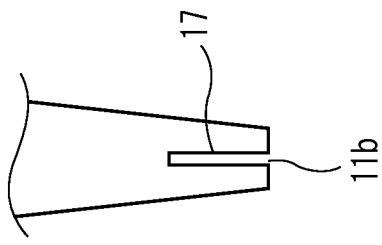

A configuration may be employed where, as shown in FIG. 5C, ear-like placement members 18 are formed in the vicinity of the opening 11b in the tip end of the pipette member 10.

According the configuration of the modification, when the pipette member 10 is attached to the container 20 in a state where the tissue 30 is scooped by the tip end of the pipette member 10 and then placed on the placement members 18, the tissue 30 can be disposed in a predetermined position of a bottom portion of the internal space 20c without difficulty. Therefore, the stirring process can be smoothly performed. The shape and size of the placement members 18 may be adequately determined in accordance with the tissue 30 to be handled.

A configuration may be employed where, as shown in FIG. 6A, in a state where the pipette member 10 is attached to the container 20, the opening 11b in the tip end of the pipette member 10 is placed in a position which is deviated from the central axis C1 of the container 20. In other words, a configuration may be employed where the central axis C2 of the opening 11b is inclined with respect to the central axis C1 of the container 20.

In order to obtain such a configuration, an adequate configuration may be employed. For example, the tip end portion 11a of the body 11 in the pipette member 10 may have a bent shape, or the shape of the holding member 15 may be made asymmetric about the central axis C1, so that the tip end portion 11a has an inclined posture.

According to the configuration of the modification, when the pressurization force for stirring is applied to the pipette member 10, a liquid flow ejected from the opening 11b impinges on the inner wall of the internal space 20c to form a flow which may swirl up the tissue 30 stickingky deposited on a bottom portion. This causes the tissue 30 to be easily sucked to the opening 11b, and therefore the cell isolation process by stirring can be smoothly performed.

In order to achieve similar effects, a configuration may be employed where, as shown in FIG. 6B, the central axis C1 of the container 20 is inclined with respect to the vertical direction V in a state where the cell isolation instrument is connected to the cell isolation apparatus.

In order to obtain such a configuration, an adequate configuration may be employed. For example, a bent portion may be disposed in the lid member 13 which is connected to the nozzle 40 of the cell isolation apparatus, and the body 11 and the container 20 may have a posture which is inclined with respect to the vertical direction V.

A further configuration may be employed where, as shown in FIG. 6C, the central axis C1 of the container 20 and the central axis C2 of the opening 11b are in a parallel and non-coaxial relationship.

The embodiment has been described in order to facilitate understanding of the invention, and is not intended to limit the invention. It is a matter of course that the invention may be changed or improved without departing the spirit thereof, and includes equivalent embodiments.

In the pipette member 10, the lid member 13 is not always essential. A configuration may be employed where the body 11 includes, in the side of the basal end, an opening which is to be connected to the nozzle 40 of the cell isolation apparatus, and the passage 14 of the body 11 is partitioned by the filter 12 into apart for stirring (first part) and a part for recovering the cell suspension (second part). In this case, the filter 12 is adhered or welded to an adequate position of the passage 14. If possible, the filter may be molded integrally with the body 11.

When, as in the embodiment, the pipette member 10 is configured so as to include the body 11 and the lid member 13, however, the filter 12 is easily disposed in a predetermined position, and therefore the assembly workability is improved.

It is not always required that the filter 12 is adhered or welded to the lid member 13 so as to cover the opening 13e. For example, a configuration may be employed where the filter 12 which is larger in diameter than the small-diameter portion 13b of the lid member 13 is fixed to a predetermined position by sandwiching the filter between the inner surface of the opening 11d of the body 11 and the outer surface of the small-diameter portion 13b of the lid member 13. In other words, when at least part of the filter 12 is in contact with the lid member 13, the above-described assembly easiness can be ensured.

The tip end portion 11a of the body 11 is not always required to have a tapered shape. The size of the opening 11b of the body 11 can be appropriately determined. When, as in the embodiment, the size of the opening 11b of the body 11 is set so as to be smaller than the opening 13d of the 11d member 13, however, it is possible to obtain a strong liquid flow during the stirring process.

What is claimed is:

1. A pipette member to be attachable to a container capable of accommodating a tissue and a liquid, the pipette member used for isolating cells from the tissue by stirring, the pipette member comprising:
   a tapered cylinder member which taper to a tip end which includes a first opening formed at the tip end, wherein the first opening to be accommodated in the container, and a second opening opposite the first opening that is to be connected to a cell isolation apparatus, and in which a passage for communicating the first opening with the second opening is defined;
   a filter member which is disposed inside the cylinder member between the first opening and the second opening, and which separates the passage into a first part that includes the first opening, and a second part that includes the second opening, wherein during the stirring a suction process and an ejection process are repeated; and
   a lid member which defines a part of the second opening, wherein at least a part of the filter member is in contact with the lid member.

2. The pipette member according to claim 1, wherein a position of the filter member is determined so that a first suction force which is applied for the stirring by the cell isolation apparatus causes only air to pass through the filter member, and, in a case where a second suction force which is larger than the first suction force is applied by the cell isolation apparatus, the liquid containing the isolated cells passes through the filter member.

3. The pipette member according to claim 1, wherein the first opening is smaller in diameter than the second opening.

4. The pipette member according to claim 1, wherein a slit which communicates with the passage is formed in a vicinity of the first opening of the cylinder member.

5. The pipette member according to claim 1, wherein a placement member on which the tissue can be placed is provided in a vicinity of the first opening of the cylinder member.

6. The pipette member according to claim 1, wherein, in a state where the pipette member is attached to the container, the first opening is placed in a position which is deviated from a central axis of the container.

7. The pipette member according to claim 1, wherein the filter member allows a material which is smaller than isolated cells, to pass through.

8. A cell isolation instrument comprising:
   A container capable of accommodating a tissue and a liquid; and
   a pipette member attached to the container, and used for isolating cells from the tissue by stirring, the pipette member comprising:
       a tapered cylinder member which taper to a tip end which includes a first opening formed at the tip end, wherein the first opening to be accommodated in the container, and a second opening opposite the first opening that is to be connected to a cell isolation apparatus, and in which a passage for communicating the first opening with the second opening is defined;
       a filter member which is disposed inside the cylinder member between the first opening and the second opening, and which separates the passage into a first part that includes the first opening, and a second part that includes the second opening, wherein during the stirring a suction process and an ejection process are repeated; and
       a lid member which defines a part of the second opening, wherein at least a part of the filter member is in contact with the lid member.

9. The cell isolation instrument according to claim 8, wherein a position of the filter member is determined so that a first suction force which is applied for the stirring by the cell isolation apparatus causes only air to pass through the filter member, and, in a case where a second suction force which is larger than the first suction force is applied by the cell isolation apparatus, the liquid containing the isolated cells passes through the filter member.

10. The cell isolation instrument according to claim 8, wherein the first opening is placed in a position which is deviated from a central axis of the container.

11. The cell isolation instrument according to claim 8, wherein, in a state where the cell isolation instrument is attached to the cell isolation apparatus, a central axis of the container is inclined with respect to a vertical direction.

12. The cell isolation instrument according to claim 8, wherein a dried reagent is placed in a bottom portion of the container.

13. The pipette member according to claim 1, wherein the filter member is configured such that a first suction force which is applied for stirring by the cell isolation apparatus causes only air to pass through the filter member, and wherein when the cell isolation apparatus continues suction, the liquid containing the isolated cells passes through the filter member and unwanted tissue pieces are filtered out by the filter member and the liquid containing desired isolated cells is obtained in the second part.

14. The cell isolation instrument according to claim 8, wherein the filter member is configured such that a first suction force which is applied for stirring by the cell isolation apparatus causes only air to pass through the filter member, and wherein when the cell isolation apparatus continues suction, the liquid containing the isolated cells passes through the filter member and unwanted tissue pieces are filtered out by the filter member and the liquid containing desired isolated cells is obtained in the second part.

15. The cell isolation instrument of claim 1, wherein the cylinder member is configured such that when the liquid flows through the cylinder member, a velocity of the liquid passing the first opening is greater than a velocity of the liquid passing the second opening, such that, during operation, fluid exits and enters the first opening in a manner that causes the tissue and liquid located in the container to be stirred.

16. The cell isolation instrument of claim 8, wherein the container is configured to hold the tissue at a bottom of the container during operation, and the cylinder member is configured such that all of the liquid located in cylinder member enters and exits the cylinder member through the first opening and the second opening, and the first opening is configured such that liquid entering and exiting the first opening is directed in a direction along a longitudinal axis of the cylinder member, and wherein the longitudinal axis of the cylinder member intersects with the bottom of the container such that, during operation, the liquid stirs the tissue located at the bottom of the cylinder member when the liquid exits and enters the first opening.

17. The cell isolation instrument of claim 16, wherein, during operation, the liquid passes the first opening at a first velocity and passes the second opening at a second velocity, the first velocity being greater than the second velocity, such that the liquid stirs the tissue in the container when ejected and then sucked back into the first opening.

18. The pipette member of claim 15, wherein the cylinder member is configured such that all of the liquid located in the cylinder member enters and exits the cylinder member through the first opening and the second opening.

19. The pipette member according to claim 1, wherein the first opening has a central axis that is substantially collinear with a longitudinal axis of the cylinder member.

* * * * *